(12) United States Patent
Halter et al.

(10) Patent No.: US 10,973,610 B2
(45) Date of Patent: Apr. 13, 2021

(54) ELECTRICAL IMPEDANCE SENSING DENTAL DRILL SYSTEM CONFIGURED TO DETECT CANCELLOUS-CORTICAL BONE AND BONE-SOFT TISSUE BOUNDARIES

(71) Applicant: THE TRUSTEES OF DARTMOUTH COLLEGE, Hanover, NH (US)

(72) Inventors: Ryan Halter, Lyme, NH (US);
Rebecca Butler, Hanover, NH (US);
Michael Salin, Lower Gwynedd, PA (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 16/491,567

(22) PCT Filed: Mar. 8, 2018

(86) PCT No.: PCT/US2018/021486
§ 371 (c)(1),
(2) Date: Sep. 5, 2019

(87) PCT Pub. No.: WO2018/165390
PCT Pub. Date: Sep. 13, 2018

(65) Prior Publication Data
US 2020/0375695 A1    Dec. 3, 2020

Related U.S. Application Data

(60) Provisional application No. 62/468,490, filed on Mar. 8, 2017, provisional application No. 62/475,724, filed on Mar. 23, 2017.

(51) Int. Cl.
*A61C 5/44* (2017.01)
*A61C 8/00* (2006.01)
(Continued)

(52) U.S. Cl.
CPC .......... *A61C 5/44* (2017.02); *A61B 17/1615* (2013.01); *A61B 17/1626* (2013.01);
(Continued)

(58) Field of Classification Search
CPC .......... A61B 17/1615; A61B 17/1617; A61B 17/1626; A61B 17/1628; A61B 17/1633;
(Continued)

(56) References Cited

U.S. PATENT DOCUMENTS 5,653,812 A    8/1997  Petrmichl et al.
8,092,457 B2   1/2012  Oettinger et al.
(Continued)

OTHER PUBLICATIONS

Bolger et al. (2006) "A preliminary study of reliability of impedance measurement to detect iatrogenic initial pedicle perforation (in the porcine model)," Eur. Spine J., vol. 15, No. 3, pp. 316-320.
(Continued)

*Primary Examiner* — Eric S Gibson
(74) *Attorney, Agent, or Firm* — Lathrop GPM LLP

(57) ABSTRACT

A dental drill system with electrical-impedance sensing indicates when a bit of the drill system approaches cortical-cancellous bone, or bone-soft tissue interfaces. The drill system has a dental drill handset having a cannula bearing electrically coupled to a drilling bit, the drilling bit having an electrically insulated portion and an exposed portion. The cannula bearing is coupled to an electrical impedance spectroscopy sensing device configured to measure impedance between the cannula bearing of the dental drill handset and a ground plate, and a processing system uses EIS measurements to distinguish when the bit of the drill system approaches cortical- or cancellous bone, or bone-soft tissue interfaces.

10 Claims, 4 Drawing Sheets

(51) Int. Cl.
*A61B 17/16* (2006.01)
*A61B 17/00* (2006.01)

(52) U.S. Cl.
CPC ........ *A61B 17/1633* (2013.01); *A61C 8/0089* (2013.01); *A61B 2017/00026* (2013.01); *A61B 2017/00831* (2013.01)

(58) Field of Classification Search
CPC ........... A61B 2017/00026; A61B 2017/00831; A61C 8/0089
See application file for complete search history.

(56) References Cited

U.S. PATENT DOCUMENTS

| | | |
|---|---|---|
| 2002/0031745 A1 | 3/2002 | Kumar et al. |
| 2005/0119660 A1 | 6/2005 | Bourlion et al. |
| 2006/0241628 A1 | 10/2006 | Parak |
| 2014/0094808 A1 | 4/2014 | Herndon |
| 2014/0141385 A1 | 5/2014 | Taub |
| 2016/0296242 A1 | 10/2016 | Pak et al. |

OTHER PUBLICATIONS

Bolger et al. (2007) "Electrical conductivity measurement: A new technique to detect iatrogenic initial pedicle perforation," Eur. Spine J., vol. 16, No. 11, pp. 1919-1924.

Dai et al. (2014) "Drilling electrode for real-time measurement of electrical impedance in bone tissues," Ann. Biomed. Eng., vol. 42, No. 3, pp. 579-588.

Gabriel et al. (1996) "The dielectric properties of biological tissues: I. Literature survey," Phys. Med. Biol., vol. 41, No. 11, pp. 2231-2249.

Gabriel et al. (1996) "The dielectric properties of biological tissues : II. Measurements in the frequency range 10 Hz to 20 GHz," Phys. Med. Biol., vol. 41, pp. 2251-2269.

Gabriel et al. (1996) "The dielectric properties of biological tissues: III. Parameteric models for the dielectric spectrum of tissues," Phys. Med. Biol., vol. 41, pp. 2271-2293.

Grill (1999) "Electrical and optical properties of diamond-like carbon," Thin Solid Films, vol. 355, pp. 189-193.

Honglertkongsakul et al. (2010 "Electrical and optical properties of diamond-like carbon films deposited by pulsed laser ablation," Diam. Relat. Mater., vol. 19, No. 7-9, pp. 999-1002.

Myers et al. (1995) "Measurement of Vertebral Cortical Integrity During Pedicle Exploration for Intrapedicular Fixation," Spine (Phila. Pa. 1976)., vol. 20, No. 2, pp. 144-148.

Saha et al. (1995) "Comparison of the electrical and dielectric behavior of wet human cortical and cancellous bone tissue from the distal tibia," J. Orthop. Res., vol. 13, No. 4, pp. 524-532.

Singh et al. (1984) "Electrical Properties of Bone—a review," Clin. Orthop. Relat. Res., No. 186, pp. 249-271.

Thomson et al. (1991) "Biocompatibility of diamond-like carbon coating," Biomaterials, vol. 12, No. 1, pp. 37-40.

International Patent Application No. PCT/US2018/021486; International Search Report and Written Opinion dated May 23, 2018; 5 pgs.

European Patent Application No. 18763237.7; Extended European Search Report and Opinion dated Nov. 18, 2020; 7 pgs.

ELECTRICAL IMPEDANCE SENSING DENTAL DRILL SYSTEM CONFIGURED TO DETECT CANCELLOUS-CORTICAL BONE AND BONE-SOFT TISSUE BOUNDARIES

CLAIM TO PRIORITY

The present application is a 35 U.S.C. § 371 filing of International Application No. PCT/US2018/021486, filed 8 Mar. 2018, which claims priority to U.S. Provisional Patent Application No. 62/475,724 filed 23 Mar. 2017. The present application also claims priority in U.S. Provisional Patent Application No. 62/468,490 filed 8 Mar. 2017. The entire contents of both provisional applications cited in this paragraph are incorporated herein by reference.

GOVERNMENT INTEREST

This invention was made with government support under grant no. 1 R41 DE024938-01 awarded by the National Institutes of Health. The government has certain rights in the invention.

BACKGROUND

Bone typically has two significantly different forms, cortical bone and cancellous bone. Cortical bone is typically found at surfaces of bone including in joints, as well as major portions of the shaft of long bones, and other areas that may be under high stress. Cortical, or compact, bone lines the outer surfaces of all bone and is denser and more structured in nature than cancellous bone. It is organized into tightly-packed osteons, each consisting of a Haversian canal (approximately 50 microns in diameter) at the center surrounded by concentric rings of matrix. Cancellous bone has a spongy structure, forming a mesh network that supports and conveys loads to and from cortical bone Cancellous bone, also referred to as trabecular or spongy bone, is found on the inside of long bones and the jaw (maxilla and mandible) bones and primarily provides light-weight, more flexible, structural support than cortical bone. It is composed of trabeculae ordered into a honeycomb-like structure and pores within cancellous bone are often filled with marrow and blood vessels.

Physical and biological properties of cortical and cancellous bone differ because of the differences in bone structure. In particular, because of the greatly different porosity of these bone types, penetration and adhesion of adhesives, the degree to which a screw or nail will hold in the bone, and growth rates of bone into porous implanted objects differ between cortical and cancellous bone.

Bone remodels throughout life. Where cortical bone lies over cancellous bone, thickness of the cortical bone varies with genetics, childhood nutritional and exercise history, age and health of a patient, as well as past medical history including fractures, periodontal disease, tooth extractions, muscle usage and weight born on the bone, and other factors. Surgeons must expect variation in bone structure between patients. In the mandible and maxilla, specifically, clinicians characterize the bone in dental implant sites according to the Lekholm and Zarb classification to determine the chance of implant success. There are four types, ranging from homogenous cortical bone, to a combination of cortical and cancellous bone, to almost entirely low density cancellous bone. Which classification depends on where the implant site is located (i.e. in the anterior region vs. premolar vs. molar) and patient characteristics.

Bone, and particularly bones of the head including the mandible and maxilla, may be penetrated by nerves and arteries, typically through foramen, or openings, through the bone. These nerves and arteries are critical structures as injury to them has potential to cause loss of sensation in parts of the mouth or face, or to cause necrotic degradation of parts of the bone. For example, the inferior alveolar nerve (IAN) penetrates through the mandible.

When performing surgery, including oral surgery, it is desirable for the surgeon to be aware of the type and dimensions of bone and surrounding structures, including critical structures, in which he is working. The surgeon may need to modify surgical techniques, such as the depth and trajectory of drilling, according to the dimensions, type, and thickness of layers of bone the surgeon is working with, to remain in bone to avoid penetrating adjacent structures like sinuses such as the maxillary sinus and nerves such as, the IAN.

One common dental surgery procedure is placement of an anchor implant to which abutments or dentures may be attached. This procedure requires drilling bone to form an initial osteotomy, or cavity within the bone, into which the implant is placed.

When performing an initial osteotomy, a surgeon may drill through a first layer of cortical bone before reaching cancellous bone, must drill deeply enough into the bone to give the implant good bonding surfaces, yet ensure the drill does not penetrate a thin distal layer of cortical bone to prevent such surgical complications as infections or neurosensory disturbances that result from drilling through the maxilla into a maxillary sinus cavity or into a nerve or blood vessel.

SUMMARY

A dental drill system with electrical-impedance-spectroscopy sensing configured to indicate whether a bit of the drill system is in adjacent cortical or cancellous bone, is approaching a cancellous/cortical bone interface, or is approaching a bone/soft tissue interface includes a dental drill having in its handset a cannulated bit, the cannulated bit having an insulating coating covering the entire surface except for a portion of distal surface of the cutting edge; a cannula bearing electrically coupled to an uninsulated interior of a cannula of the cannulated bit, an electrical impedance spectroscopy sensing (EIS) measurement and calculation unit configured to measure impedance between the cannula bearing and a ground plate or return electrode, and a processing system configured to distinguish changes in electrical properties indicating an approaching cancellous/cortical bone interface or a change as the bit of the drill system approaches an interface between cancellous and cortical bone, or a bone-soft tissue interface.

A method of detecting approach of a bit to cortical bone or soft tissue while drilling bone with the bit includes providing an insulating coating extending from near a cutting end of the bit to a handset end of the bit, contacting the bit with a cannular bearing, driving a voltage-limited current between the bit and a ground plate at least one alternating current frequency; measuring voltage and phase between bit and ground plate; determining impedance from measured voltage and phase; and generating an alarm when the impedance changes, indicating an interface between bone and soft tissue or between cancellous and cortical bone.

DETAILED DESCRIPTION OF THE EMBODIMENTS

The vastly different cellular constituents of cortical and cancellous bone provide a spectrum of electrical charge carrying and charge storage capabilities, which are represented by electrical conductivity ($\sigma$) and permittivity ($\varepsilon$), respectively ($\sigma$ and $\varepsilon$ are inversely related to resistance and reactance). When recording these electrical properties over a broad range of frequencies (100's of Hz to 10's of MHz), as is done in Electrical Impedance Spectroscopy (EIS), cortical and cancellous bone have been reported to differ significantly. Studies have investigated electrical impedance measurements in pedicle screw insertion into vertebrae and have shown that electrical property differences between cancellous and cortical bone can be used to guide surgeons through vertebral bone.

We describe herein an EIS device integrated with a drill configured for drilling holes in bone, such as may be required for a variety of surgical procedures in dentistry and some non-dental surgeries. The drill is particularly configured for measuring bioimpedance spectra in vivo during the initial osteotomy of dental implant procedures. The drill is particularly adapted for measuring the electrical impedance spectra of bony structures in vivo as the drill is advanced into the structure. This EIS drill provides real-time feedback to the clinician, as either an auditory or visual signal, allowing the clinician to stop drilling before perforation of the cortical layer occurs (enabling immediate clinical intervention if necessary). In a particular embodiment, the drill is a dental drill.

Figure 1:
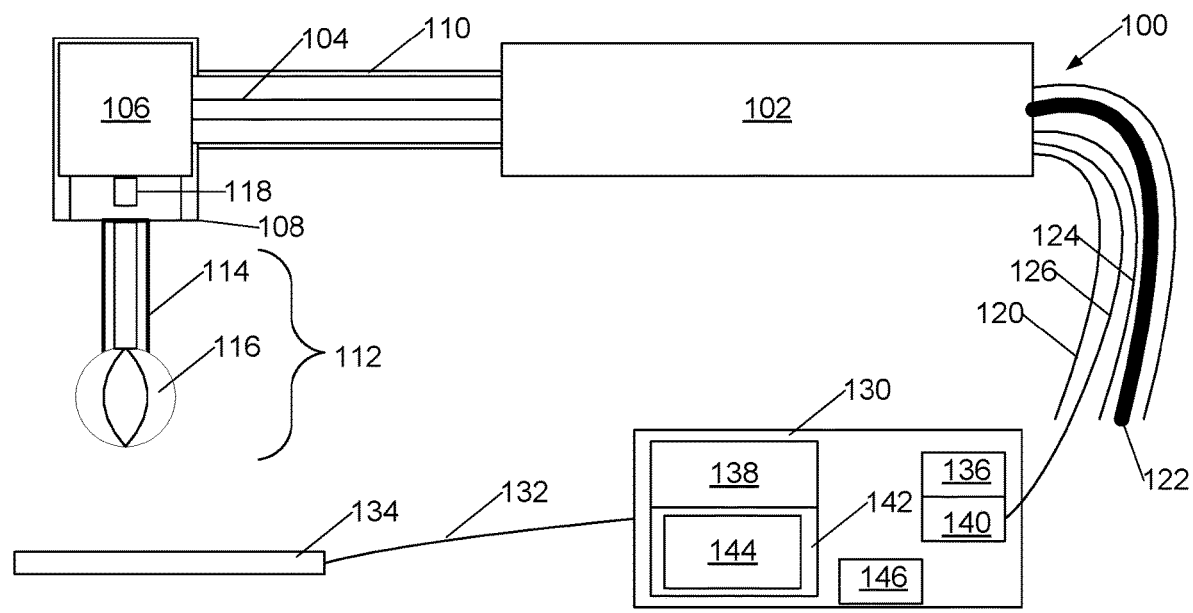
FIG. 1 is a block diagram of the drilling system with electrical impedance spectroscopic sensing.
Figure 6:
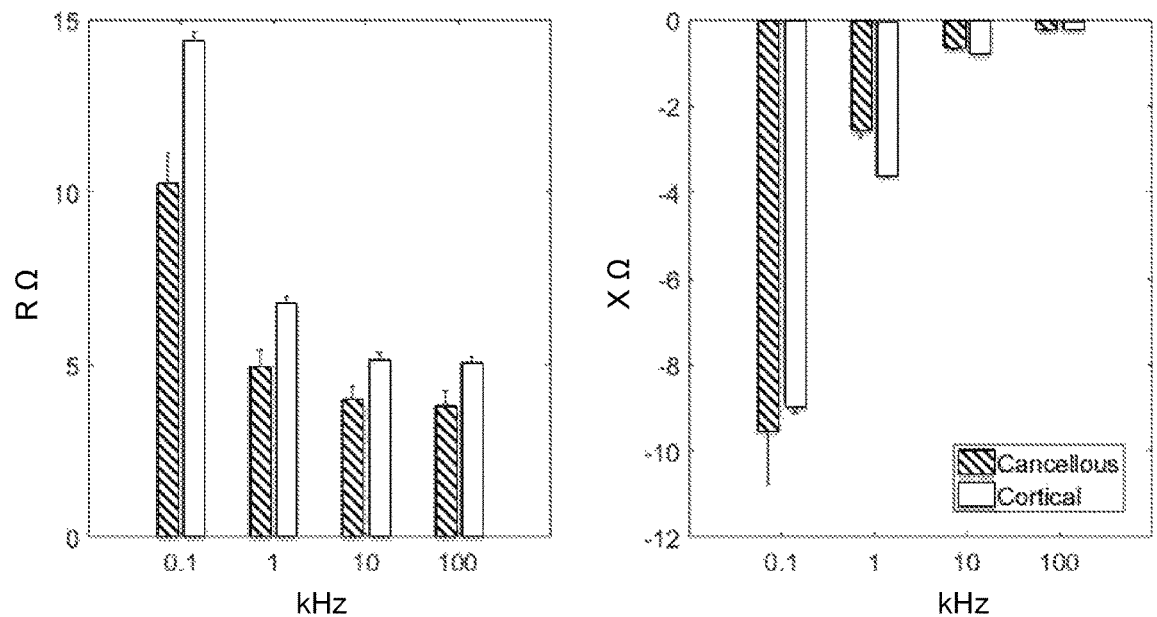
FIG. 6 illustrates contrast of normalized mean resistance and reactance of cancellous and cortical bone measured with a prototype integrated on a standard Nobel Biocare Drill with a drill bit in ex vivo bone.
Figure 7:
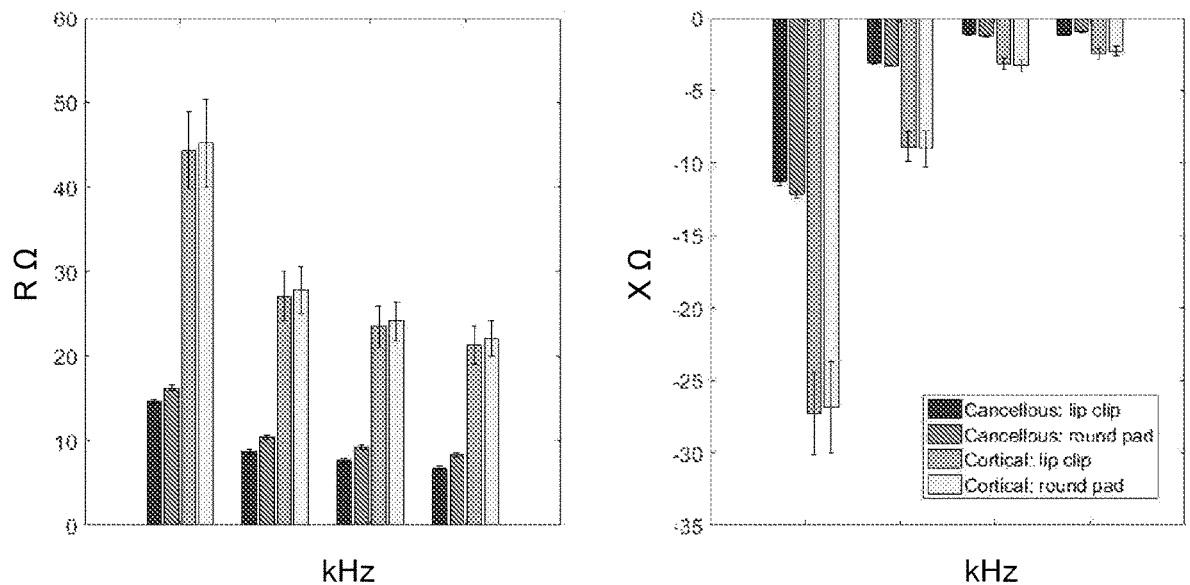
FIG. 7 illustrates contrast of normalized mean resistance and reactance of cancellous and cortical bone measured with a prototype integrated on a standard Nobel Biocare Drill with a drill bit in fresh, in situ, bone.

The EIS-sensing drill system 100 is illustrated in FIG. 1. A dental drill handset 102 contains a high-speed motor and driveshaft 104 leading to a right-angle bevel gear unit 106, the bevel gear unit and a housing 110 of the driveshaft 104 being insulated with an insulating coating 108. Coupled to the bevel gear unit is a drilling bit 112 having an insulated portion 114 and a bare, cutting, portion 116. Bare cutting portion 116 is a portion of a ball-like burr in some embodiments and a tip of a twist-drill bit in other embodiments; the insulated portion extends from the cutting portion to a handset end of the bit that is mechanically coupled to into a dental drill handset. Within bevel gear unit 106 is a cannular bearing 118 electrically coupled to bit 112. Handset 102 has an umbilical tubular housing 120 holding a tube 122 for irrigation fluid, an electrical drive wire for the motor of handset 102, and an electrical wire adapted for coupling the cannular bearing 118 to an electrical impedance spectroscopy (EIS) measurement and calculation unit 130, EIS measurement and calculation unit 130 also couples through another wire 132 to a second electrode plate 134. Within EIS measurement and calculation unit 130 are an EIS stimulus unit 136 capable of operation at 100, 1000, 10000, and 100000 Hz under direction of processor 138 and an EIS impedance measurement unit 140. In alternative embodiments, EIS impedance measurement and calculation unit 130 is capable of operation at two or more frequencies in the 100 Hz to 1 MHz range. Processor 138 has a memory 142 with EIS measurement firmware and classifier firmware 144, the classifier firmware adapted to use EIS measurements to determine whether bit 112 is drilling in cancellous or cortical bone and to announce which bone type bit 112 is in using indicator 146.

Figure 2:
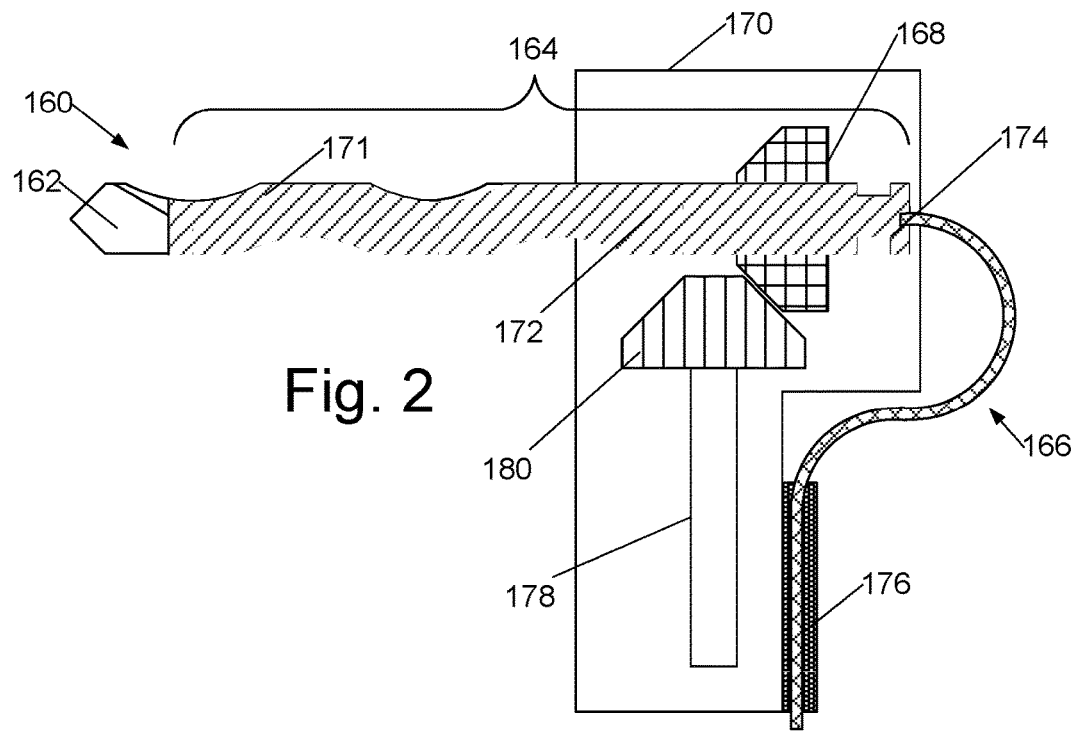
FIG. 2 is a sketch of a drill bit of the current drilling system.

A twist-drill embodiment is illustrated in more detail in FIG. 2. A twist-drill bit 160 has a bare or uninsulated end 162 with cutting edges that may contact and drill holes in bone. Bit 160 also has an electrically insulated portion 164 bearing a coating of diamond-like carbon (DLC), a coating that is both very hard such that it wears little while holes are being drilled in bone, and electrically of high resistivity, the coating of DLC extends throughout the remainder of the exterior of bit 160 to the drill end of bit 160, including portions that engage bevel gear of drill head 170, and including portions over flutes 171. Bit 160 also has an uninsulated axial hole 172 extending from drill end of bit into, but not all the way through, the bit.

Within the axial hole 172 and in electrical contact with the uninsulated surface of bit 160 in that hole is an uninsulated end portion 174 of cannular bearing 166. Cannular bearing 166 extends from bit's 160 end through insulation 176 to electronics EIS measurement and calculation unit 130 (FIG. 1). Drive shaft 178 and bevel gear 180 rotate to drive bevel gear 168 of drill head 170 to rotate bit 160 to drill the holes into bone.

Figure 3:
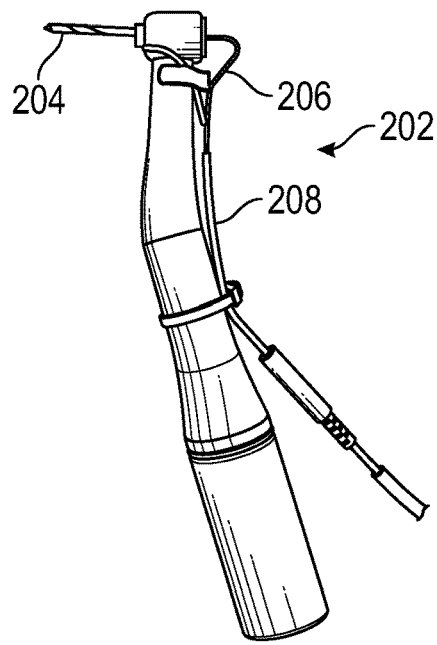
FIG. 3 is a photograph showing an embodiment of a drill having a bit with cannular bearing attached.
Figure 4:
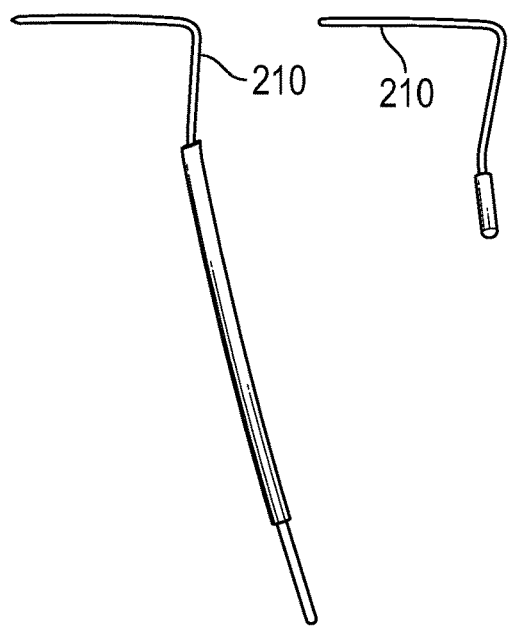
FIG. 4 is an illustration of electrical resistance and reactance of cancellous and cortical bone samples measured with a prototype integrated on a Nobel Biocare Drill with a 2 mm twist bit.
Figure 5:
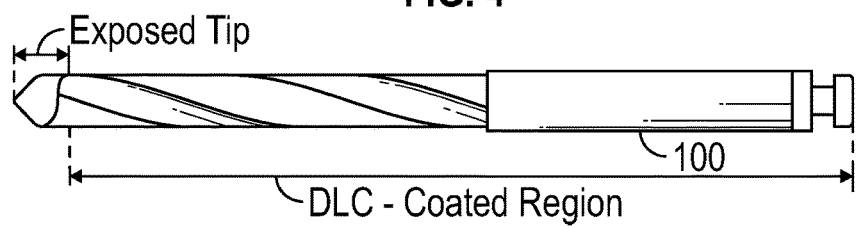
FIG. 5 is a photograph of a DLC-coated drill bit having a bare cutting end.

FIGS. 1 and 2 are schematics, FIG. 3 is a photograph showing an embodiment of an experimental drill 202 having a bit 204 with cannular bearing 206 and insulated lead 208 attached, and FIG. 4 is a photograph showing a pair of uninstalled cannular bearings 210. In an embodiment, cannular bearings 210, 206, are formed of stainless steel.

In various embodiments the uninsulated end portion 174 of bit 160, or uninsulated ball portion of bit 116, is from one to three millimeters in length.

Operation of the EIS Drill System:

The EIS measurement and calculation unit, drill, and bit with cannular bearing together form the EIS drilling system. Positioning the bearing 206 within the drill bit's cannula does not decrease the surgical working space and still allows for irrigation through the intra-cannular channel or around the exterior surface of the drill bit. The cannular bearing connects to a lead that interfaces with the impedance analyzer. Similarly, the return electrode 134 (FIG. 1) connects to another lead that interfaces with the impedance analyzer. A voltage-limited, alternating current (AC) current is applied between the two electrode elements at several frequencies and the voltage and phase induced between them is recorded. From these measurements, impedance is calculated as the ratio of voltage to current.

Impedance (Z) is calculated as the ratio of the measured voltage to the injected current; we regard the impedance as a complex quantity, consisting of a real resistive component (R) and an imaginary reactive component (X), according to the equation, $Z=R+jX$. The electronics box computes an R and X measurement at each frequency being tested. From those we compute impedance, conductivity, resistivity, and the like.

We have shown in previous experiments in ex vivo and in situ pig femurs that cortical bone has a higher resistivity and impedance than cancellous bone. The ratio of cortical-to-cancellous resistivity ranged from 1.28-1.48 in ex vivo bone and from 2.82-2.94 in fresh in situ bone. As a result, we expect that, as the drill bit moves through cancellous bone towards a cortical interface we will see an increase in impedance/resistivity as we approach that interface.

In an embodiment, the EIS measurement and calculation unit is configured to provide a visual and/or aural alarm when the drill bit approaches cortical bone.

Clinical use of this device involves using the drill to create the initial osteotomy (hole in the bone) marked for implant insertion. Electrical properties, specifically the resistance and reactance of the bone, are recorded over a single or multiple frequencies as the drill is advanced into the bone. These measurements will be input into a real-time classification unit used to sense an approaching tissue transition (i.e. the cancellous-cortical interface). A visual or auditory signal that increases in repetition rate, based on the changing impedance, will be used as clinician feedback.

We have collected a significant dataset of ex vivo and in situ electrical properties of cortical and cancellous bone and have shown significant impedance contrast between the two bone types.

In the ex vivo experiment, we positioned standard cannulated drill bits three millimeters deep into 10 samples each of cortical and cancellous bone freshly harvested from swine and recorded impedance from 100 Hz-1 MHz at 41 frequencies. We demonstrated that there are significant R and X differences ($p<0.05$) between the two bone types with contrasts in resistance of 41%, 37%, 29%, and 32% at 0.1 kHz, 1 kHz, 10 kHz, and 100 kHz, respectively. These trends, recorded with our prototype, are similar to those reported previously for cancellous and cortical bone.

In the in situ experiment, we used a custom DLC-coated drill bit to record impedances from 40 samples each of cortical and cancellous bone in the femurs of pigs 30 minutes after euthanasia. We demonstrated that there are significant R and X differences ($p<0.001$) between the tissue types, with a maximum resistance contrast of ~300% at 100 kHz and a maximum reactance contrast of ~250% at 1 kHz.

The electrical impedance sensing is responsive not just to the tissue type the tip is in, but to tissue types near the tip. The system can therefore watch for impedance changes as the drill penetrates bone and generate an alarm when the impedance changes indicate the tip is approaching a cancellous-cortical bone interface, or when the tip is approaching a bone-soft tissue interface; bone-soft tissue interfaces include interfaces between bone and blood vessels, nerves, sinus lining, muscles, and other non-ossified tissues.

Features

Features of this dental drill system with electrical-impedance-spectroscopy sensing include:
1) a coated dental drill bit as the sensing or driving electrode,
2) a Diamond-Like-Carbon (DLC) coating to insulate all but the distal few millimeters of the drill bit,
3) an intra-cannular bearing to interface the drill bit with the impedance-sensing module,
4) collecting impedance measurements at multiple frequencies for this particular surgical drill application, and
5) extending the interface detection feature beyond pure threshold detection.

In addition, by interfacing our system to the dental implant drill through the cannular space, we do not need to augment the drill in any way nor do we decrease the working volume available to the surgeon. Irrigation is still possible despite the presence of the bearing, allowing for surgeons to continue using cannulated drill bits as they were intended.

DLC coatings are designed to have extremely high hardness (4000-9000 HV), high resistivity (up to $10^6$ Ω-cm), and are bio-compatible. By applying this insulating coating to the majority of the drill bit and leaving only the distal 1-3 mm exposed for sensing, we provide more robust and repeatable impedance measurements that are not dependent on drill bit depth into the material. While some prior art includes provisions for an insulating material applied to the drilling device, they do not specify the type of insulating material, nor do they leave an area on the distal end exposed for sensing.

Collecting impedance measurements at multiple frequencies, instead of a single frequency, has the potential for better classification between cancellous and cortical bone. The increased number of measurements will allow us to explore additional features that can be used to contrast the two bone types. Most prior art is based on threshold detection at a single frequency to alert clinicians of an approaching tissue interface. We use multiple features and algorithms to find an optimal combination to use for interface detection.

Figure 8:
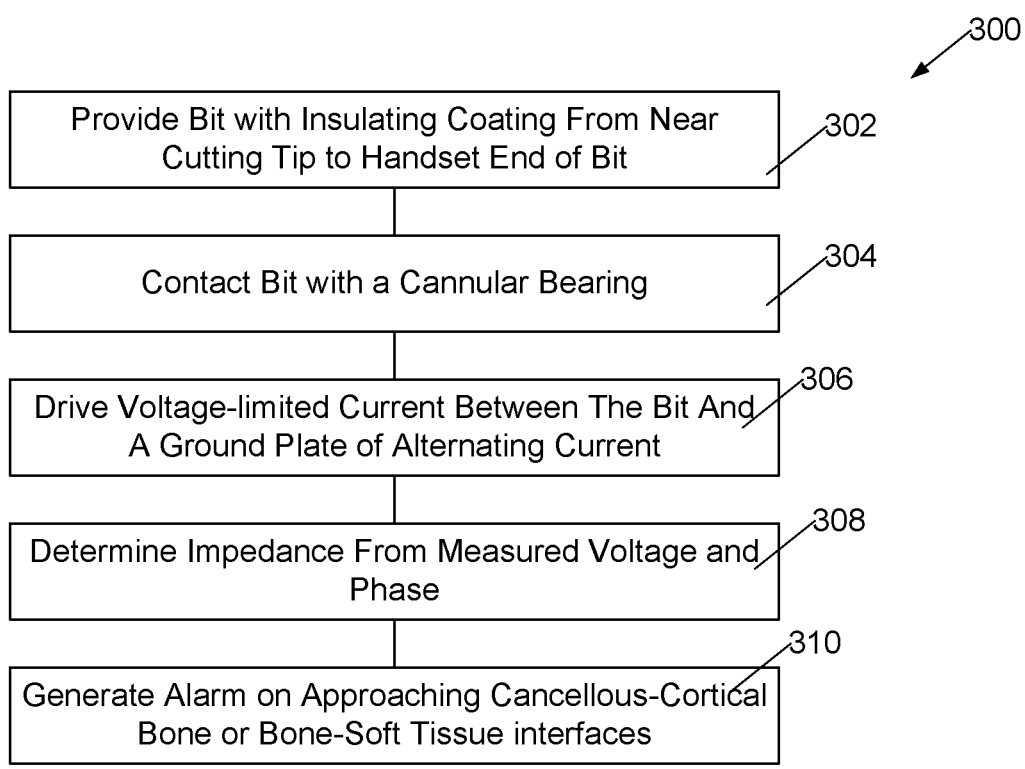
FIG. 8 is a flowchart of a method of detecting approach of a drill bit to cortical bone during surgical procedures.

In an embodiment, the method of detecting approach of a bit to cortical bone while drilling bone with the bit includes providing 302 (FIG. 8) an insulating coating extending from near a cutting end of the bit to a handset end of the bit, and contacting 304 the bit with a cannular bearing. Then the EIS measurement and calculation unit drives 306 a voltage-limited current between the bit and a ground plate at least one alternating current frequency and measures voltage and phase, then determines 308 impedance from measurements of voltage and phase between bit and ground plate; and generates 310 an alarm when the impedance changes indicating approach to cancellous-cortical bone or bone-soft tissue interfaces.

In an alternative embodiment, a contact portion of the handset end of the bit is bare of the DLC insulating coating, and the handset is modified to provide electrical contact from the EIS measurement and calculation device to that bare portion of the handset end of the bit while isolating the remainder of the drill handset from the EIS measurement and calculation device.

Combinations of Features

A dental drill system designated A with electrical-impedance sensing (EIS) configured to indicate whether a bit of the drill system is approaching a cancellous-cortical bone interface or a bone-soft tissue interface includes a dental drill having in its handset a cannulated bit, the cannulated bit having an insulating coating extending from near a cutting end of the bit to a handset end of the bit a cannula bearing electrically coupled to an uninsulated interior of a cannula of the cannulated bit, an EIS measurement and calculation unit configured to measure impedance between the cannula bearing and a ground plate, and a processing system configured to distinguish when the bit of the drill system approaching a cancellous-cortical bone or bone-soft tissue interface.

A dental drill system designated AA including the dental drill system designated A wherein the electrically insulated portion of the drilling bit is insulated with a diamond-like carbon (DLC) coating.

A dental drill system designated AB including the dental drill system designated A or AA wherein EIS measurement and calculation unit provides a voltage-limited current at each of a plurality of frequencies and measures a resulting voltage and phase.

A dental drill system designated AC including the dental drill system designated A, AA, or AB wherein the EIS measurement and calculation unit is configured to provide a visual and/or aural alarm when the drill bit approaches cortical bone.

A dental drill system designated AD including the dental drill system designated A, AA, AB, or AC wherein the EIS measurement and calculation unit is configured to measure impedance at least two frequencies in the range 100 to 100000 Hertz.

A method designated B of detecting approach of a bit to cortical bone, or approach of a bit to bone-soft tissue interface, while drilling bone with the bit includes providing an insulating coating extending from near a cutting end of the bit to a handset end of the bit, contacting the bit with a cannular bearing; driving a voltage-limited current between the bit and a ground plate at least one alternating current frequency; measuring voltage and phase between bit and ground plate; and determining impedance from measured voltage and phase; and generating an alarm when the impedance changes indicating approach to cancellous-cortical bone interfaces or bone-soft tissue interfaces.

A method designated BA including the method designated B wherein the voltage-limited current is driven at multiple frequencies between 100 and 100000 Hertz.

CONCLUSION

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:
1. A dental drill system with electrical-impedance sensing (EIS) configured to indicate whether a bit of the drill system is approaching a cancellous-cortical bone interface or a bone-soft tissue interface comprising:
 a dental drill having in its handset a cannulated bit, the cannulated bit having an insulating coating extending from near a cutting end of the bit to a handset end of the bit, a cannula bearing electrically coupled to an uninsulated interior of a cannula of the cannulated bit,
 an EIS measurement and calculation unit configured to measure impedance between the cannula bearing and a ground plate, and
 a processing system configured to distinguish when the bit of the drill system approaches a cancellous-cortical bone or bone-soft tissue interface.

2. The dental drill system of claim 1 wherein the insulating coating of the drilling bit is insulated with a diamond-like-carbon (DLC) coating.

3. The dental drill system of claim 2, wherein the EIS measurement and calculation unit is configured to measure impedance at least two frequencies in the range of 100 to 100000 Hertz.

4. The dental drill system of claim 1 the wherein EIS measurement and calculation unit provides a voltage-limited current at each of a plurality of frequencies and measures a resulting voltage and phase.

5. The dental drill system of claim 4, wherein the EIS measurement and calculation unit is configured to measure impedance at least two frequencies in the range of 100 to 100000 Hertz.

6. The dental drill system of claim 1 wherein the EIS measurement and calculation unit is configured to provide a visual and/or aural alarm when the drill bit approaches cortical bone.

7. The dental drill system of claim 6, wherein the EIS measurement and calculation unit is configured to measure impedance at least two frequencies in the range of 100 to 100000 Hertz.

8. The dental drill system of claim 1 wherein the EIS measurement and calculation unit is configured to measure impedance at least two frequencies in the range of 100 to 100000 Hertz.

9. A method of detecting approach of a bit to cortical bone, or approach of a bit to bone-soft tissue interface, while drilling bone with the bit comprising:
 providing an insulating coating extending from near a cutting end of the bit to a handset end of the bit;
 contacting the bit with a cannular bearing;
 driving a voltage-limited current between the bit and a ground plate at least one alternating current frequency;
 measuring voltage and phase between the bit and ground plate;
 determining impedance from the measured voltage and phase; and
 generating an alarm when the impedance changes indicating approach to cancellous-cortical bone interfaces or bone-soft tissue interfaces.

10. The method of claim 9 wherein the voltage-limited current is driven at multiple frequencies between 100 and 1,000,000 Hertz.

* * * * *